US010422740B2

United States Patent
Marta et al.

(10) Patent No.: US 10,422,740 B2
(45) Date of Patent: Sep. 24, 2019

(54) DUAL WAVELENGTH SOURCE GAS DETECTOR

(71) Applicant: Honeywell International Inc., Morris Plains, NJ (US)

(72) Inventors: Teresa M. Marta, White Bear Lake, MN (US); Martin Willett, Waterlooville (GB); Bernard Fritz, Eagan, MN (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 15/202,324

(22) Filed: Jul. 5, 2016

(65) Prior Publication Data

US 2017/0307518 A1  Oct. 26, 2017

Related U.S. Application Data

(60) Provisional application No. 62/325,848, filed on Apr. 21, 2016.

(51) Int. Cl.
  *G01N 21/31* (2006.01)
  *G01N 21/3504* (2014.01)
  *G01N 21/39* (2006.01)

(52) U.S. Cl.
  CPC .......... *G01N 21/31* (2013.01); *G01N 21/314* (2013.01); *G01N 21/3151* (2013.01); *G01N 21/3504* (2013.01); *G01N 21/39* (2013.01); *G01N 2021/3148* (2013.01); *G01N 2021/3181* (2013.01); *G01N 2201/062* (2013.01);
  (Continued)

(58) Field of Classification Search
  CPC ......... G01N 21/31; G01N 2201/06113; G01N 2201/062; G01N 2201/10
  USPC .................................................. 356/432–444
  See application file for complete search history.

(56) References Cited

U.S. PATENT DOCUMENTS 4,560,873 A  12/1985  McGowan et al.
5,995,529 A  11/1999  Kurtz et al.
(Continued)

FOREIGN PATENT DOCUMENTS

| CN | 107328722 A | 11/2017 |
| EP | 3236238 A1 | 10/2017 |
| GB | 2245058 A | 12/1991 |

OTHER PUBLICATIONS

Honeywell Application Note "Comparison of optical detection systems for Infrared (IR) Hydrocarbon gas detection", APN0078V1_06-13, downloaded on Jun. 13, 2014, 5 pages.
(Continued)

*Primary Examiner* — Tri T Ton
(74) *Attorney, Agent, or Firm* — Wick Phillips Gould & Martin, LLP (57) ABSTRACT

Devices, methods, systems, and computer-readable media for a dual wavelength source gas sensor are described herein. One or more embodiments include a gas sensor, comprising: a dual wavelength source to transmit a first wavelength and a second wavelength via an optical path, wherein a gas is present through the optical path, a detector to receive the first wavelength and the second wavelength via the optical path, and a computing device coupled to the detector to determine an determine a signal intensity for the first wavelength and the second wavelength.

19 Claims, 4 Drawing Sheets

(52) U.S. Cl.
CPC .............. *G01N 2201/06113* (2013.01); *G01N 2201/10* (2013.01)

(56) References Cited

U.S. PATENT DOCUMENTS

| | | | | |
|---|---|---|---|---|
| 8,964,185 | B1* | 2/2015 | Luo | G01N 33/0036 356/436 |
| 2004/0000643 | A1* | 1/2004 | Karlsson | G01N 21/3504 250/339.13 |
| 2004/0256562 | A1* | 12/2004 | Scheying | G01N 21/3151 250/339.06 |
| 2010/0078560 | A1 | 4/2010 | Basham | |
| 2011/0255087 | A1* | 10/2011 | Alexander | G01N 21/53 356/338 |
| 2012/0287418 | A1* | 11/2012 | Scherer | G01N 21/61 356/51 |
| 2014/0091219 | A1 | 4/2014 | Schaefer | |
| 2015/0014541 | A1 | 1/2015 | Depenheuer et al. | |
| 2016/0005921 | A1 | 1/2016 | Suchalkin et al. | |
| 2016/0054281 | A1* | 2/2016 | Smeeton | G01N 21/532 250/373 |

OTHER PUBLICATIONS

Das, "Infrared light emitting device with two color emission", Solid State Electronics, 2010, 4 pages.

Jung, Seungyong, Dissertation entitled "Mid Infrared III-V Semiconductor Emitters and Detectors", Stony Brook University, Dec. 2012, 154 pages.

Europe Patent Application No. 17165601.0, Extended European Search Report, dated Aug. 28, 2017, 15 pages.

Europe Patent Application No. 17165601.0, Communication pursuant to Article 94(3) EPC, dated Aug. 9, 2018, 10 pages.

Europe Patent Application No. 17165601.0, Communication pursuant to Article 94(3) EPC, dated Feb. 8, 2018, 11 pages.

* cited by examiner

DUAL WAVELENGTH SOURCE GAS DETECTOR

TECHNICAL FIELD

The present disclosure relates to methods, devices, systems, and computer-readable media for a dual wavelength source gas sensor.

BACKGROUND

Extended instrument run times between battery charges are highly desirable in many gas detector applications. As the power consumption of a typical 4-gas instrument is dominated by the flammable gas detecting channel, this power consumption and battery life can be important issues.

Both accepted methods for flammable detection (catalytic and optical) traditionally suffer from high power consumption. And, as such, current battery capacities or their form factors may be unacceptable limitations for some gas detecting operations.

Developments in areas such as micro-hotplate substrates have driven down pellistor powers from ~200 mW to ~20 mW, but further major reductions are unlikely without unacceptable impacts on response time of the device. Bulb-based optical systems give the greatest in-band power levels, with resulting advantages for detection performance. Such systems have fallen from powers of ~250 to ~50 mW, but are believed to be unable to be reduced significantly further.

Most microelectromechanical systems (MEMs) thermal sources do not offer a particularly favorable power/speed combination. Attention has, therefore, turned to a new generation of light emitting diode (LED) sources in the 3 microns to 5 microns region. These devices can operate at much faster frequencies and output powers that approach or exceed the in-band optical outputs of bulb-based optical systems but with average power consumptions in the mW region or below.

Further, the trend toward smaller, slimmer portable instruments demands lower sensor profiles rather than the more traditional cylindrical industry standard 4-series types. The accompanying restrictions on available optical path-length place greater emphasis on the stability and performance of the detection systems. Therefore, the ability to provide a reference which reduces the impact of non-gas effects on the sensor output is of growing importance.

DETAILED DESCRIPTION

Devices, methods, systems, and computer-readable media for a dual wavelength source gas sensor are described herein. One or more embodiments include a gas sensor, comprising: a dual wavelength source to transmit a first wavelength and a second wavelength via an optical path, wherein a gas is present through the optical path, a detector (e.g., optical detector, IR detector, etc.) to receive the first wavelength and the second wavelength via the optical path, and a computing device coupled to the detector to determine a signal intensity for the first wavelength and the second wavelength. As used herein the signal intensity can be sample gas species density level computed from a measured transmission intensity level through the sample gas at each wavelength band. As used herein, the first wavelength and the second wavelength can represent a range of wavelengths emitting from a source.

The dual wavelength source gas sensor of the present disclosure describes a robust referencing system for optical gas sensors which are compatible with the characteristics of having low power consumption and small physical size while not incurring unacceptable cost.

A second source wavelength can be used as part of a referencing scheme to make an optical gas sensor that does not require calibration or may require less calibration and is resistant to drift in span and zero. Typically, these wavelength bands are selected by dispersive or, more commonly, nondispersive elements (such as narrow band interference filters) from within the wide spectral emission of a broadband source such as a blackbody emitter. Conventionally, one band or wavelength (e.g., acting as a sample wavelength) would be chosen to overlap a favorable spectral absorption region of the target gas whereas the other band or wavelength (e.g., acting as a reference wavelength) would be in the closest available region devoid of relevant absorptions from the target species or known interferents. In this way, the system aims to compensate for any effects not due to the target species and so provide a robust, reliable measurement.

For this aim to be fully met, the light in each channel should ideally traverse an identical optical path. However, if separate wavelength selective elements are required for each channel, or if separate spatially separated detectors are needed for each band, this requirement can be significantly compromised. A single broadband detector can be used to overcome some of these drawbacks, but each wavelength emission must then be individually controlled. This cannot be achieved with a single broadband source unless more complex arrangements, such as shutters, beam splitters, or other moving parts, are used, but these arrangements are undesirable for other reasons.

Further, two source and two detector arrangements may be employed. However, these arrangements can significantly increase the cost and complexity of the optical arrangement to an extent which is often not compatible with small, low cost designs. A solution according to an embodiment of the present disclosure comprises single source and detector components which are able to separately emit and measure the selected wavelength bands. Collinear sample and reference beams allow the use of simple but effective optical designs.

The dual wavelength source (e.g., laser or LED) can be constructed such that each source (e.g., a sample wavelength and a reference wavelength) is separately addressable, where each could be operated at a different frequency and deconvolved at the detector. For example, the source to detect the gas of interest may run at a regular frequency to meet the performance requirements while the reference source is activated only when needed, for example, possibly at less frequent intervals to save power. In some examples, the dual wavelength source transmits the first wavelength and the second wavelength at different frequencies, duty cycles, and pulse patterns.

One advantageous approach according to an embodiment of the present disclosure is to utilize two or more stacked laser or LED sources which provide separately controllable emission in two different wavebands. Such a structure can be designed to allow the emitter made up of the lower layers of the structure to emit through the emitter structure of the upper layers, and this has been demonstrated with available materials (e.g., III-V materials). In other approaches, a scanning emitter or a tunable emitter can be utilized as a wavelength source.

Provided the dual wavelength source is constructed such that each emitter can be separately addressed, it is quite feasible to operate the two sources at different frequencies, duty cycles, and pulse patterns. In principle, this allows a single broadband detector to deconvolve signals from the two different wavebands and deliver the signal and reference signals from identical or closely spaced optical paths, as desired.

Alternatively, such a source could be used with two or more stacked detectors. In such an embodiment, a first layer (e.g., an upper layer) allows transmission of the second radiation band to a second layer (e.g., an underlying detector).

These examples can also enable a device as a single dual wavelength package that is likely to cost less than two individual devices. Further, there is also the potential to manage or reduce power consumption by operating only one wavelength output at a time. In some examples, a combined package or single device can be advantageous over multiple devices. For example, a combined package can be advantageous when applying thermal control for the combined package since there can be relatively less overall consumption and a closer correlation compared to two individual devices.

It is also conceivable that a shorter wavelength reference, which would be more sensitive to detecting particulates (e.g., as a means of monitoring system health) could be employed. In such an embodiment, a dual band photodetector (e.g., targeting the designed operating wavelengths of the source) could be used as the detector. In some examples, a reference wavelength and a sample wavelength can be utilized to compare an intensity of the reference wavelength to an intensity of the sample wavelength. In some examples, an observed lowering of the intensity of the reference wavelength without an observed lowering of the intensity of the sample wavelength can be utilized to determine a presence of particulates as described herein.

In some examples, the dual wavelength source gas sensor as described herein can be utilized to identify molecules within a gas based on absorption properties of the gas. In some examples, the dual wavelength source can be a light emitting diode (LED) source to lower power consumption. In some examples, the dual wavelength source gas sensor can utilize a single optical pathway for a reference wavelength and a sample wavelength. In some examples, the reference wavelength and the sample wavelength can be received by a single detector coupled to a computing device.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that process changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit corresponds to the drawing figure number and the remaining digits identify an element or component in the drawing. Similar elements or components between different figures may be identified by the use of similar remaining digits.

As used herein, "a" or "a number of" something can refer to one or more such things. For example, "a number of devices" can refer to one or more devices. Additionally, the designator "N", as used herein, particularly with respect to reference numerals in the drawings, indicates that a number of the particular feature so designated can be included with a number of embodiments of the present disclosure.

Figure 1:
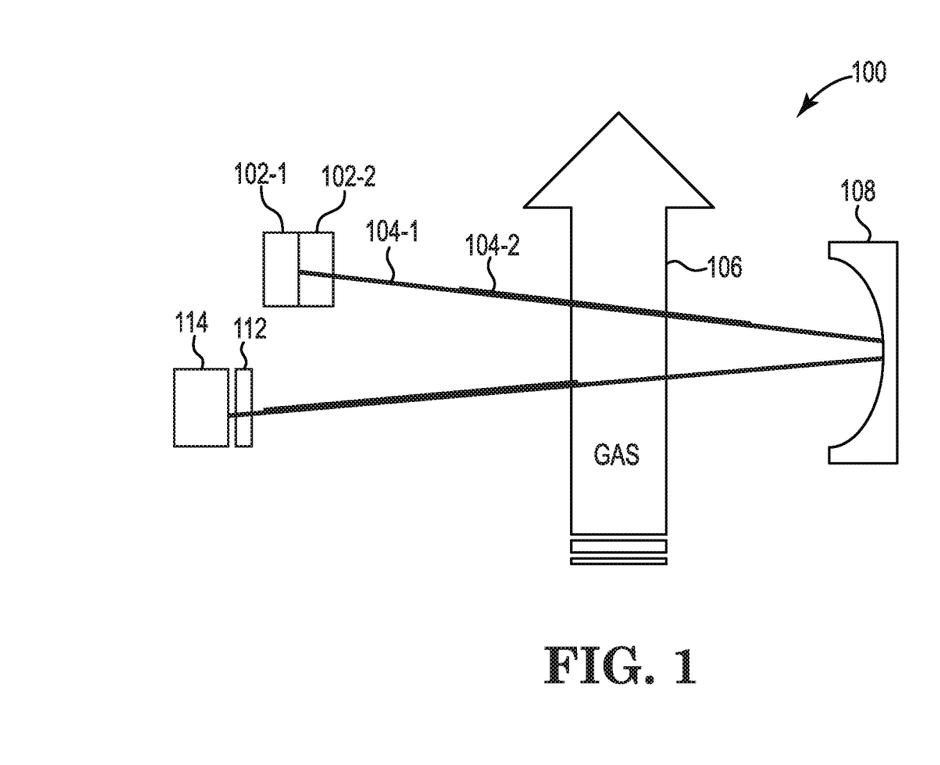
FIG. 1 is an example of a system for a dual wavelength source gas sensor consistent with the present disclosure.

FIG. 1 is an example of a system 100 for a dual wavelength source gas sensor consistent with the present disclosure. In some examples, the system 100 can be utilized as a relatively low-power optical based flammable gas sensor. In some examples, the system 100 can include a dual wavelength source 102-1, 102-2. In some examples, the dual wavelength source 102-1, 102-2 can be utilized to generate a first wavelength 104-1 and a second wavelength 104-2.

In some examples, the first wavelength 104-1 can be a sample wavelength and the second wavelength 104-2 can be a reference wavelength. In some examples, the sample wavelength can be a wavelength within a predicted absorption range of molecules within the gas 106. For example, the system 100 can utilize a sample wavelength that can be a wavelength within an absorption range of hydrocarbon gas, such as methane. In this example, the system 100 can be utilized to determine the presence or absence of a flammable gas based on an intensity level of the sample wavelength detected at a detector 114. In some examples, the reference wavelength can be a wavelength outside the predicted absorption range of molecules of the target gas 106 and/or outside a predicted absorption range of exterior interferent gases. In some examples, the reference wavelength can be utilized to identify absorption from sources other than the sample molecules within the gas 106.

In some examples, the second wavelength 104-2 or reference wavelength can be utilized to detect changes in source intensity or particulates or obstructions within the optical path that may cause unexpected absorption. In some examples, the second wavelength 104-2 or reference wavelength can be utilized to identify a system failure. For example, the second wavelength 104-2 or reference wavelength can be utilized to identify the presence of an obstruction in the optical path by comparing the first wavelength 104-1 to the second wavelength 104-2. In some examples, a computing device coupled to the detector 114 can utilize the second wavelength 104-2 to monitor an intensity of the dual wavelength source 102-1, 102-2. For example, when an intensity of the first wavelength 104-1 and the second wavelength 104-2 is detected, it can be determined that an obstruction exists or that there has been a change in the dual wavelength source 102-1, 102-2.

In some examples, the first wavelength 104-1 and the second wavelength 104-2 can be separately addressable. For example, a computing device coupled to the dual wavelength source 102-1, 102-2 can transmit the first wavelength 104-1 separately from the second wavelength 104-2. In some examples, the dual wavelength source 102-1, 102-2 can alternate between the first wavelength 104-1 and the second wavelength 104-2 at a defined rate. In some examples, the dual wavelength source 102-1, 102-2 can transmit the first wavelength 104-1 at a first rate and the second wavelength 104-2 at a second rate.

As used herein, transmitting the wavelength at a defined rate includes transmitting a wavelength pulse a number of times over a time period. In some examples, the dual wavelength source 102-1, 102-2 can transmit the first wavelength 104-1 at a relatively higher rate compared to the second wavelength 104-2. For example, the first wavelength 104-1 can be a sample wavelength that is transmitted more frequently over the period of time compared to the second wavelength 104-2 that is utilized as a reference wavelength. That is, the dual wavelength source 102-1, 102-2 can transmit the first wavelength 104-1 at a first interval and can transmit the second wavelength 104-2 at a second interval that is different than the first interval. In some examples, the first interval can occur more frequently than the second interval.

In some examples, the system 100 can include an optical device 108 (e.g., reflective device, refractive element, lens, mirror, etc.). In some examples, the optical device 108 can be a mirror that can receive the first wavelength 104-1 and/or the second wavelength 104-2 from the dual wavelength source 102-1, 102-2 and direct the first wavelength 104-1 and/or the second wavelength 104-2 to a detector 114. In some examples, the detector 114 can receive the first wavelength 104-1 and/or the second wavelength 104-2 from the same optical path. In some examples, the dual wavelength source 102-1, 102-2 can transmit the first wavelength 104-1 and/or the second wavelength 104-2 through the gas 106 to the optical device 108 and the optical device 108 can transfer the first wavelength 104-1 and/or the second wavelength 104-2 through the gas 106 to the detector 114. In some examples, the detector 114 can be a dual band photodetector.

In some examples, the dual wavelength source 102-1, 102-2 can be positioned on a first side of the gas 106 and the optical device 108 can be positioned on a second side of the gas 106. In some examples, the dual wavelength source 102-1, 102-2 can transmit the first wavelength 104-1 and the second wavelength 104-2 through the gas 106 a first time and the optical device 108 can direct the first wavelength 104-1 and the second wavelength 104-2 through the gas 106 a second time to the detector 114.

In some examples, the system 100 can include a filter 112 between the detector 114 and the optical device 108. In some examples, the filter 112 can be designed to filter specific portions of the emitting wavelengths from the dual wavelength source 102-1, 102-2 prior to being received at the detector 114. In some examples, the filter 112 can be utilized to filter both the first wavelength 104-1 and/or the second wavelength 104-2. For example, the filter 112 can be an adjustable filter that can be altered by a computing device coupled to the detector 114 and/or the filter 112. In some examples, the filter 112 can be altered at the same or similar rate as the dual wavelength source 102-1, 102-2 switches between transmitting the first wavelength 104-1 and the second wavelength 104-2. In some examples, the filter 112 can be a Fabry Perot Interference Filter that is tunable over a wavelength range.

In some examples, the detector 114 can be a single detector that is responsive to both the first wavelength 104-1 and the second wavelength 104-2. In some examples, the first wavelength 104-1 and the second wavelength 104-2 can be wavelengths that are relatively far apart and the detector 114 can be responsive to both the first wavelength 104-1 and the second wavelength 104-2. In these examples, the filter 112 may be removed from the system 100. In some examples, the computing device coupled to the detector 114 can perform a deconvolution process on the first wavelength 104-1 and the second wavelength 104-2 when the first wavelength 104-1 and the second wavelength 104-2 are received at the detector 114.

Figure 2:
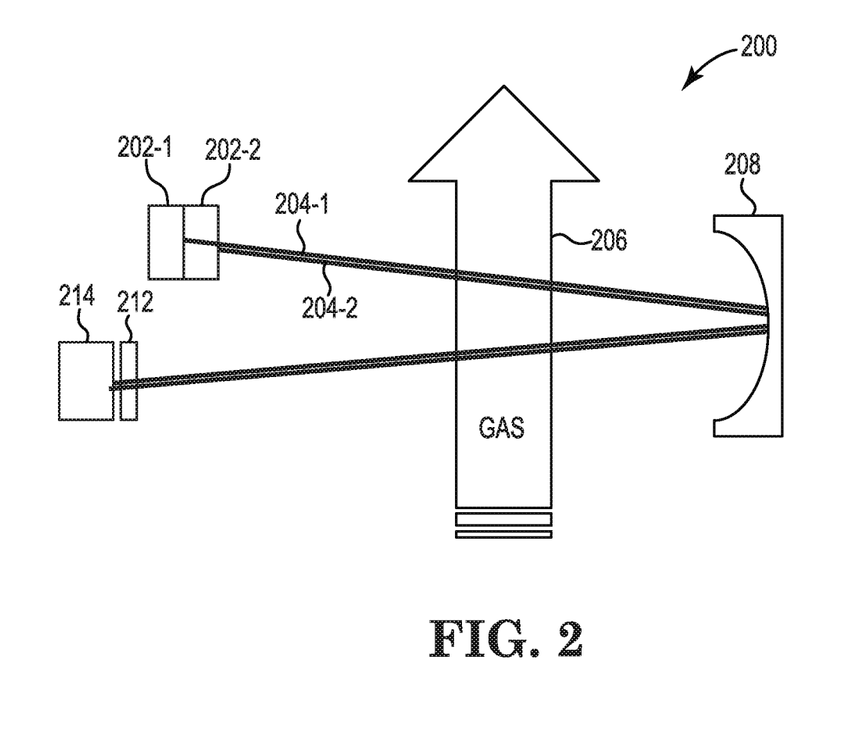
FIG. 2 is an example of a system for a dual wavelength source gas sensor consistent with the present disclosure.

FIG. 2 is an example of a system 200 for a dual wavelength source gas sensor consistent with the present disclosure. In some examples, the system 200 can be utilized similarly to system 100 as referenced in FIG. 1. In some examples, the system 200 can be utilized as a relatively low-power optical based flammable gas sensor. In some examples, the system 200 can detect molecules within the gas 206 while utilizing relatively less power and utilizing a relatively smaller physical footprint compared to previous systems and methods.

In some examples, the system 200 can include a dual wavelength source 202-1, 202-2. In some examples, the dual wavelength source 202-1, 202-2 can include a stacked source. As used herein, a stacked source includes a first source 202-1 and a second source 202-2 that can transmit a first wavelength 204-1 and a second wavelength 204-2 in a substantially similar direction (e.g., similar optical path, substantially parallel path, etc.). For example, the dual wavelength source 202-1, 202-2 can include a first source 202-1 to transmit a first wavelength 204-1 on a first optical path. In this example, the dual wavelength source 202-1, 202-2 can include a second source 202-2 that is coupled to the first source 202-1 to transmit a second wavelength 204-2 on a second optical path. In some examples, the first optical path can be substantially similar with the second optical path. In some examples, the stacked source can provide more than two wavelengths and/or wavelength ranges. That is, the stacked source can include N number of sources stacked similarly to the dual wavelength source 202-1, 202-2 as illustrated in FIG. 2. In these examples, the stacked source can provide N number of wavelengths or wavelength ranges. In some examples, that stacked source can include a corresponding stacked detector with N detectors as described herein.

In some examples, the first wavelength 204-1 can be a sample wavelength and the second wavelength 204-2 can be a reference wavelength. In some examples, the sample wavelength can be a wavelength within a predicted absorption range of molecules within the gas 206 (e.g., target gas, target gas species, etc.). For example, the system 200 can utilize a sample wavelength that can be a wavelength within an absorption range of hydrocarbons (e.g., methane, etc.). In this example, the system 200 can be utilized to detect the presence or absence of a flammable gas based on an absorption or intensity (e.g., absorption of particular wavelengths within the sample wavelength range, etc.) of the sample wavelength detected at a detector 214. In some examples, the reference wavelength can be a wavelength outside the predicted absorption range of target gas molecules or known interferents within the gas 206. In some examples, the reference wavelength can be utilized to identify absorption from gases other than the target molecules within the gas 206.

In some examples, the second wavelength 204-2 or reference wavelength can be utilized to detect the presence of particulates or obstructions within the optical path that may cause a potential for a spurious alarm or error in the indicated value (e.g., over reading, under reading, etc.) of the target gas. In some examples, the second wavelength 204-2 or reference wavelength can be utilized to identify a system failure. For example, the second wavelength 204-2 or reference wavelength can be utilized to identify when there are particles or obstructions contributing to a decrease in signal strength of the first wavelength 204-1 or sample wavelength.

In some examples, the system 200 can include an optical device 208. In some examples, the optical device 208 can be a mirror that can receive the first wavelength 204-1 and/or the second wavelength 204-2 from the dual wavelength source 202-1, 202-2 and direct the first wavelength 204-1 and/or the second wavelength 204-2 to a detector 214. In some examples, the detector 214 can receive the first wavelength 204-1 and/or the second wavelength 204-2 from their respective optical paths (e.g., substantially parallel optical paths, first optical path and second optical path, substantially similar, etc.). In some examples, the dual wavelength source 202-1, 202-2 can transmit the first wavelength 204-1 and/or the second wavelength 204-2 through the gas 206 to the optical device 208 and the optical device 208 can transfer the first wavelength 204-1 and/or the second wavelength 204-2 through the gas 206 to the detector 214. In some examples, the detector 214 can be a dual band photodetector.

In some examples, the dual wavelength source 202-1, 202-2 can be positioned on a first side of the gas 206 and the optical device 208 can be positioned on a second side of the gas 206. In some examples, the dual wavelength source 202-1, 202-2 can transmit the first wavelength 204-1 and the second wavelength 204-2 through the gas 206 a first time and the optical device 208 can direct the first wavelength 204-1 and the second wavelength 204-2 through the gas 206 a second time to the detector 214.

In some examples, the system 200 can include a filter 212 between the detector 214 and the optical device 208. In some examples, the filter 212 can be utilized to filter the first wavelength 204-1 and/or the second wavelength 204-2 prior to being received at the detector 214. In some examples, the filter 212 can be utilized to filter both the first wavelength 204-1 and the second wavelength 204-2. That is, the filter 212 can be an adjustable filter that can be altered with an electronic signal and controlled by a computing device coupled to the detector 214 and/or the filter 212. In some examples, the filter 212 can be a Fabry Perot Interference Filter that is tunable over a wavelength range.

In some examples, the detector 214 can be a single detector that is responsive to both the first wavelength 204-1 and the second wavelength 204-2. In some examples, the first wavelength 204-1 and the second wavelength 204-2 can be wavelengths that are relatively far apart and the detector 214 can be responsive to both the first wavelength 204-1 and the second wavelength 204-2. In these examples, the filter 212 may be removed from the system 200.

In some examples, the dual wavelength source 202-1, 202-2 can include two or more stacked lasers, scanning emitter, or LED sources which can provide separately controllable emission in two different wavebands (e.g., first wavelength 204-1 and second wavelength 204-2, etc.). In some examples, the dual wavelength source 202-1, 202-2 can comprise an upper source and a lower source. In these examples, the upper source can transmit the first wavelength through an upper layer or upper optical path and the lower source can transmit the second wavelength through a lower layer or lower optical path. Such a structure can allow the lower source to emit through the upper layer with available materials (e.g., III-V materials). That is, in some examples, a portion of the second wavelength 204-2 can pass through the material structure emitting the first wavelength 204-1.

Figure 3:
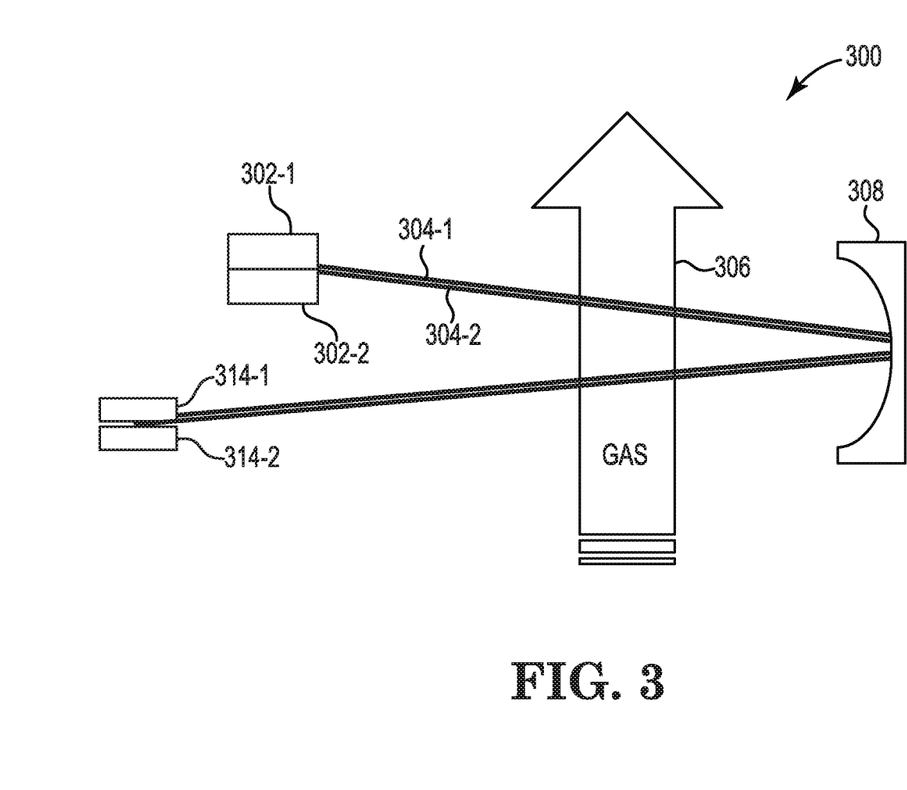
FIG. 3 is an example of a system for a dual wavelength source gas sensor consistent with the present disclosure.

FIG. 3 is an example of a system 300 for a dual wavelength source gas sensor consistent with the present disclosure. In some examples, the system 300 can be utilized similarly to system 100 as referenced in FIG. 1 and/or system 200 as referenced in FIG. 2. In some examples, the system 300 can be utilized as a relatively low-power optical based flammable gas sensor. In some examples, the system 300 can detect molecules within the gas 306 while utilizing relatively less power and utilizing a relatively smaller physical footprint compared to previous systems and methods.

In some examples, the system 300 can include a dual wavelength source 302-1, 302-2. In some examples, the dual wavelength source 302-1, 302-2 can include a stacked source. As used herein, a stacked source includes a first source 302-1 and a second source 302-2 that can transmit a first wavelength 304-1 and a second wavelength 304-2 in a substantially similar direction. For example, the dual wavelength source 302-1, 302-2 can include a first source 302-1 to transmit a first wavelength 304-1 on a first optical path. In this example, the dual wavelength source 302-1, 302-2 can include a second source 302-2 that is coupled to the first source 302-1 to transmit a second wavelength 304-2 on a second optical path. In some examples, the first optical path can be substantially similar with the second optical path.

In some examples, the first wavelength 304-1 can be a sample wavelength and the second wavelength 304-2 can be a reference wavelength. In some examples, the sample wavelength can be a wavelength within a predicted absorption range of target molecules within the gas 306. For example, the system 300 can utilize a sample wavelength that can be a wavelength within an absorption range of hydrocarbons. In this example, the system 300 can be utilized to detect the presence or absence of a flammable gas based on an absorption or intensity of the sample wavelength detected at a detector 314-1, 314-2. In some examples, the reference wavelength can be a wavelength outside the predicted absorption range of sample molecules within the gas 306 and/or outside the predicted absorption range of other interferent gases. That is, the reference wavelength can be a wavelength that is not absorbed by any gas present in the sample volume. In some examples, the reference wavelength can be utilized to identify absorption from gases other than the sample molecules or known interferents within the gas 306.

In some examples, the second wavelength 304-2 or reference wavelength can be utilized to detect particulates or obstructions within the optical path that may cause unexpected absorption. In some examples, the second wavelength 304-2 or reference wavelength can be utilized to identify a system failure. For example, the second wavelength 304-2 or reference wavelength can be utilized to monitor the source intensity and identify when there are particulates or obstructions contributing to absorption of the first wavelength 304-1 or sample wavelength.

In some examples, the system 300 can include an optical device 308. In some examples, the optical device 308 can be a mirror that can receive the first wavelength 304-1 and/or the second wavelength 304-2 from the dual wavelength source 302-1, 302-2 and direct the first wavelength 304-1 and/or the second wavelength 304-2 to a detector 314-1, 314-2. In some examples, the detector 314-1, 314-2 can be a stacked detector. As used herein, a stacked detector can include a first detector 314-1 coupled to a second detector 314-2. The stacked detector can be configured to receive the first wavelength 304-1 at the first detector 314-1 and receive the second wavelength 304-2 at the second detector 314-2. In some examples, the detector 314-1, 314-2 can be a dual band photodetector.

In some examples, the detector 314-1, 314-2 can receive the first wavelength 304-1 and/or the second wavelength 304-2 from their respective optical paths (e.g., substantially parallel optical paths, first optical path and second optical path, substantially similar, etc.). In some examples, the dual wavelength source 302-1, 302-2 can transmit the first wavelength 304-1 and/or the second wavelength 304-2 through the gas 306 to the optical device 308 and the optical device 308 can transfer the first wavelength 304-1 and/or the second wavelength 304-2 through the gas 306 to a corresponding detector 314-1, 314-2.

Figure 4:
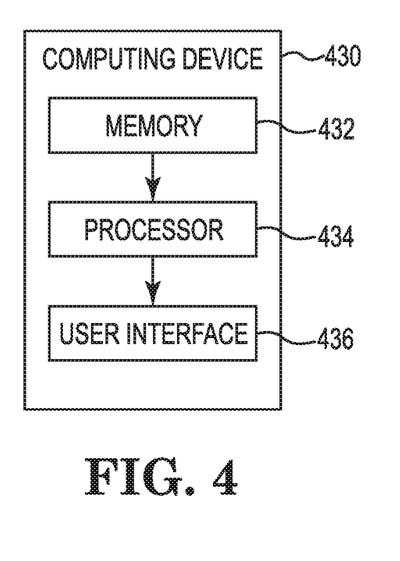
FIG. 4 is an example of a diagram of a computing device for a dual wavelength source gas sensor consistent with one or more embodiments of the present disclosure.

FIG. 4 is an example of a diagram of a computing device 430 for a dual wavelength source gas sensor consistent with one or more embodiments of the present disclosure. Computing device 430 can be, for example, an embedded system as described herein, among other types of computing devices. For example, the computing device 430 can be coupled to a sensor (e.g., detector 114 as referenced in FIG. 1, etc.).

As shown in FIG. 4, computing device 430 includes a memory 432 and a processor 434 coupled to user interface 436. Memory 432 can be any type of storage medium that can be accessed by processor 434, which performs various examples of the present disclosure. For example, memory 432 can be a non-transitory computer readable medium having computer readable instructions (e.g., computer program instructions) stored thereon.

Processor 434 executes instructions to determine presence or absence of flames and failure modes in accordance with one or more embodiments of the present disclosure. Processor 434 can also estimate the presence of the combinations of radiance of the wavelengths. Processor 434 can also execute in depth analyses computing the characteristics of the detected items for further decision making.

Further, although memory 432, processor 434 and user interface 436 are illustrated as being located in computing device 430, embodiments of the present disclosure are not so limited. For example, memory 432 can also be located internal to another computing resource (e.g., enabling computer readable instructions to be downloaded over the Internet or another wired or wireless connection). Part of the memory can be storage in a cloud storage. Processor 434 can be a cloud computer.

As shown in FIG. 4, computing device 430 can also include a user interface 436. User interface 436 can include, for example, a display (e.g., a screen, an LED light, etc.). The display can be, for instance, a touch-screen (e.g., the display can include touch-screen capabilities). User interface 436 (e.g., the display of user interface 436) can provide (e.g., display and/or present) information to a user of computing device 430.

Additionally, computing device 430 can receive information from the user of computing device 430 through an interaction with the user via user interface 436. For example, computing device 430 (e.g., the display of user interface 436) can receive input from the user via user interface 436. The user can enter the input into computing device 430 using, for instance, a mouse and/or keyboard associated with computing device 430, or by touching the display of user interface 436 in embodiments in which the display includes touch-screen capabilities (e.g., embodiments in which the display is a touch screen).

As used herein, "logic" is an alternative or additional processing resource to execute the actions and/or functions, etc., described herein, which includes hardware (e.g., various forms of transistor logic, application specific integrated circuits (ASICs), etc.), field programmable gate arrays (FPGAs), as opposed to computer executable instructions (e.g., software, firmware, etc.) stored in memory and executable by a processor.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:
1. A gas sensor, comprising:
 a dual wavelength source configured to transmit a first wavelength and a second wavelength via an optical path, wherein a gas is present through the optical path, and wherein the first wavelength and the second wavelength are separately addressable at the dual wavelength source such that the first wavelength and the second wavelength are transmitted at different frequencies;
 a detector configured to receive the first wavelength and the second wavelength via the optical path; and
 a processor coupled to the detector and configured to:
  determine a signal intensity for the first wavelength and the second wavelength;
  determine an error in the signal intensity of the first wavelength based on the signal intensity of the second wavelength; and
  generate an alarm signal based on the determined error.
2. The gas sensor of claim 1, wherein the first wavelength is a sample wavelength within an absorption range of the gas.
3. The gas sensor of claim 1, wherein the second wavelength is a reference wavelength that is outside an absorption range of sample molecules within the gas and interferent gases present within the gas.
4. The gas sensor of claim 1, wherein the dual wavelength source is a scanning emitter.
5. The gas sensor of claim 1, wherein the processor is further configured to perform a deconvolution process on the first wavelength and the second wavelength when the first wavelength and the second wavelength are received at the detector.

6. The gas sensor of claim 1, wherein the dual wavelength source is configured to transmit the first wavelength and the second wavelength at different frequencies, duty cycles, and pulse patterns.

7. The gas sensor of claim 1, wherein the processor is further configured to utilize the second wavelength to monitor source intensity.

8. The gas sensor of claim 1, wherein the detector is a dual band photodetector.

9. A system for a gas sensor, comprising:
a dual wavelength source configured to transmit a first wavelength via a first optical path and a second wavelength via a second optical path, wherein the first optical path and the second optical path are similar, and wherein the dual wavelength source is further configured to transmit the first wavelength at a first frequency and the second wavelength at a second frequency that is different than the first frequency;
a detector to receive the first wavelength and the second wavelength through a gas; and
a processor coupled to the detector and configured to:
determine a density level of the gas based on an intensity of the first wavelength and the second wavelength;
determine error in the density level based on the intensity of the second wavelength; and
generate an alarm signal based on the determined error.

10. The system of claim 9, wherein the dual wavelength source is a stacked source.

11. The system of claim 10, wherein the stacked source is configured to transmit the first wavelength, the second wavelength, and a number of additional wavelengths.

12. The system of claim 9, wherein a portion of the second wavelength passes through the first optical path.

13. The system of claim 9, wherein the dual wavelength source is a stacked laser or a stacked light emitting diode (LED).

14. The system of claim 9, wherein the detector is a stacked detector.

15. The gas sensor of claim 3, wherein the processor is configured to use an absorption of the reference wavelength to identify a system failure.

16. A system for a gas sensor, comprising:
a dual wavelength source configured to transmit a first wavelength via a first optical path and a second wavelength via a second optical path, wherein the first optical path and the second optical path are similar, and wherein the first wavelength and the second wavelength are separately addressable at the dual wavelength source such that the first wavelength and the second wavelength are transmitted at different frequencies;
a detector to receive the first wavelength and the second wavelength through a gas; and
a processor coupled to the detector and configured to:
determine a density level of the gas based on an intensity of the first wavelength and the second wavelength;
determine error in the density level based on the intensity of the second wavelength; and
generate an alarm signal based on the determined error.

17. The system of claim 16, wherein the dual wavelength source comprises a plurality of emitters, wherein a first emitter of the plurality of emitters is configured to produce the first wavelength, wherein a second emitter of the plurality of emitters is configured to produce the second wavelength, and wherein the first emitter and the second emitter are separately addressable.

18. The system of claim 16, wherein the dual wavelength source is configured to transmit the first wavelength, the second wavelength, and a number of additional wavelengths.

19. The system of claim 16, wherein dual wavelength source is a stacked source.

* * * * *